(12) United States Patent
Owen

(10) Patent No.: US 10,575,928 B2
(45) Date of Patent: Mar. 3, 2020

(54) ORTHODONTIC BRACKET RETENTION ANCHOR

(71) Applicant: Brandon Owen, Fort Collins, CO (US)

(72) Inventor: Brandon Owen, Fort Collins, CO (US)

( * ) Notice: Subject to any disclaimer, the term of this patent is extended or adjusted under 35 U.S.C. 154(b) by 0 days.

(21) Appl. No.: 15/711,996

(22) Filed: Sep. 21, 2017

(65) Prior Publication Data

US 2019/0083204 A1 Mar. 21, 2019

(51) Int. Cl.
*A61C 7/14* (2006.01)

(52) U.S. Cl.
CPC .................... *A61C 7/146* (2013.01)

(58) Field of Classification Search
CPC ...................................... A61C 7/146
USPC .................................. 433/3, 8–24
See application file for complete search history.

(56) References Cited

U.S. PATENT DOCUMENTS

| | | | |
|---|---|---|---|
| 2,716,283 A | 8/1955 | Atkinson | |
| 3,250,003 A | 5/1966 | Collito | |
| 4,243,386 A | 1/1981 | Kawaguchi | |
| 4,494,931 A | 1/1985 | Wildman | |
| 4,551,094 A | 11/1985 | Kesling | |
| 4,948,366 A | 8/1990 | Horn et al. | |
| 5,098,288 A | 3/1992 | Kesling | |
| 5,248,257 A | 9/1993 | Cannon | |
| 5,263,859 A | 11/1993 | Kesling | |
| 5,447,432 A | 9/1995 | Andreiko et al. | |
| 5,464,347 A | 11/1995 | Allesee | |
| 5,464,349 A | 11/1995 | Andreiko et al. | |
| 5,542,842 A | 8/1996 | Andreiko et al. | |
| 5,683,243 A | 11/1997 | Andreiko et al. | |
| 5,782,631 A | 7/1998 | Kesling et al. | |
| 6,015,289 A | 1/2000 | Andreiko et al. | |
| 6,206,690 B1 | 3/2001 | Vargas | |
| 6,244,861 B1 | 6/2001 | Andreiko et al. | |
| 6,247,923 B1 | 6/2001 | Vashi | |
| 6,347,939 B2 | 2/2002 | Abels | |
| 6,394,798 B1 | 5/2002 | Huff et al. | |
| 6,592,367 B2 | 7/2003 | Kyritsis | |
| 6,616,444 B2 | 9/2003 | Andreiko et al. | |
| 6,632,089 B2 | 10/2003 | Rubbert et al. | |
| 6,685,468 B1 | 2/2004 | Kesling | |
| 6,776,614 B2 | 8/2004 | Wiechmann et al. | |
| 7,033,170 B2 | 4/2006 | Cordato | |
| 7,131,836 B1 | 11/2006 | Kesling | |

(Continued)

FOREIGN PATENT DOCUMENTS

| | | |
|---|---|---|
| EP | 1 830 735 | 9/2007 |
| WO | WO 2007/087697 | 8/2007 |
| WO | 2015/052541 | 4/2015 |

OTHER PUBLICATIONS

U.S. Appl. No. 61/880,322, filed Sep. 20, 2013.

(Continued)

*Primary Examiner* — Matthew M Nelson
(74) *Attorney, Agent, or Firm* — Craig R. Miles; CR Miles P.C.

(57) ABSTRACT

Orthodontic articles such as brackets and methods for the manufacture of brackets having configurations which maintain position or resist movement or displacement during the production of or in the use of bracket placement or transfer apparatuses having a shape that matches the configuration of at least part of the patient's dental arch for use in indirect bonding techniques.

28 Claims, 9 Drawing Sheets

(56) References Cited

U.S. PATENT DOCUMENTS

| | | |
|---|---|---|
| 7,155,373 B2 | 12/2006 | Jordan et al. |
| 7,160,107 B2 | 1/2007 | Kopelman et al. |
| 7,223,099 B2 | 5/2007 | Niederwanger et al. |
| 7,229,282 B2 | 6/2007 | Andreiko et al. |
| 7,326,051 B2 | 2/2008 | Miller |
| 7,766,653 B2 | 8/2010 | Manemann et al. |
| 7,837,466 B2 | 11/2010 | Griffith et al. |
| 7,850,451 B2 | 12/2010 | Wiechmann et al. |
| 8,113,828 B1 | 2/2012 | Greenfield |
| 8,353,699 B2 | 1/2013 | Johnston |
| 8,550,814 B1 | 10/2013 | Collins |
| 8,979,528 B2 | 3/2015 | Macchi et al. |
| 9,486,299 B2 | 11/2016 | Owen |
| 9,707,057 B2 | 7/2017 | Owen |
| 2002/0010568 A1 | 1/2002 | Rubbert et al. |
| 2003/0039938 A1 | 2/2003 | Orikasa |
| 2003/0224310 A1 | 12/2003 | Andreiko |
| 2004/0115586 A1 | 6/2004 | Andreiko et al. |
| 2004/0121279 A1 | 6/2004 | Kelly |
| 2004/0219471 A1 | 11/2004 | Cleary et al. |
| 2005/0186525 A1 | 8/2005 | Abels et al. |
| 2005/0244774 A1 | 11/2005 | Abels et al. |
| 2006/0228662 A1 | 10/2006 | Lokar et al. |
| 2007/0128571 A1 | 6/2007 | Kimura |
| 2007/0259300 A1 | 11/2007 | McLaghlin et al. |
| 2007/0259302 A1 | 11/2007 | Jayawardena |
| 2008/0057459 A1 | 3/2008 | Abels et al. |
| 2008/0070184 A1 | 3/2008 | Farzin-Nia et al. |
| 2008/0311534 A1 | 12/2008 | Farzin-Nia et al. |
| 2009/0004617 A1 | 1/2009 | Oda et al. |
| 2009/0004619 A1 | 1/2009 | Oda et al. |
| 2009/0117511 A1 | 5/2009 | Minium |
| 2009/0155734 A1 | 6/2009 | Damon |
| 2009/0162807 A1 | 6/2009 | Hagenganz et al. |
| 2010/0173256 A1 | 7/2010 | Rodriguez et al. |
| 2010/0196839 A1 | 8/2010 | Stevens |
| 2010/0297569 A1 | 11/2010 | Huang et al. |
| 2011/0014583 A1 | 1/2011 | Romano et al. |
| 2011/0020762 A1 | 1/2011 | Kanomi et al. |
| 2011/0033811 A1 | 2/2011 | Swain |
| 2011/0091832 A1 | 4/2011 | Kim et al. |
| 2011/0097682 A1 | 4/2011 | Curiel et al. |
| 2011/0151391 A1 | 6/2011 | Shih et al. |
| 2011/0250556 A1 | 10/2011 | Heiser |
| 2012/0015315 A1 | 1/2012 | Wiechmann et al. |
| 2012/0107760 A1 | 5/2012 | Eichenberg |
| 2012/0225398 A1 | 9/2012 | Fallah |
| 2012/0308952 A1 | 12/2012 | Cosse |
| 2012/0322019 A1* | 12/2012 | Lewis ............... A61C 7/20 433/10 |
| 2013/0040260 A1 | 2/2013 | Bukhary |
| 2016/0000529 A1* | 1/2016 | Kim ............... A61C 7/002 433/3 |

OTHER PUBLICATIONS

PCT International Patent Application No. PCT/US2014/056679; International Search Report dated Jan. 2, 2015, 15 total pages.

PCT International Patent Application No. PCT/US2014/056679, filed Sep. 19, 2014.

PCT International Patent Application No. PCT/US14/58982, filed Oct. 3, 2014.

PCT International Patent Application No. PCT/US14/58982; International Search Report dated Jan. 14, 2015, 10 total pages.

U.S. Appl. No. 61/886,461, filed Oct. 3, 2013.

U.S. Appl. No. 15/648,305, filed Jul. 12, 2017.

U.S. Appl. No. 14/504,325, filed Oct. 1, 2014.

U.S. Appl. No. 15/627,226, filed Jun. 19, 2017.

PCT International Patent Application No. PCT/US18/49616; International Search Report and Written Opinion of the International Searching Authority dated Nov. 30, 2018, 12 pages.

* cited by examiner

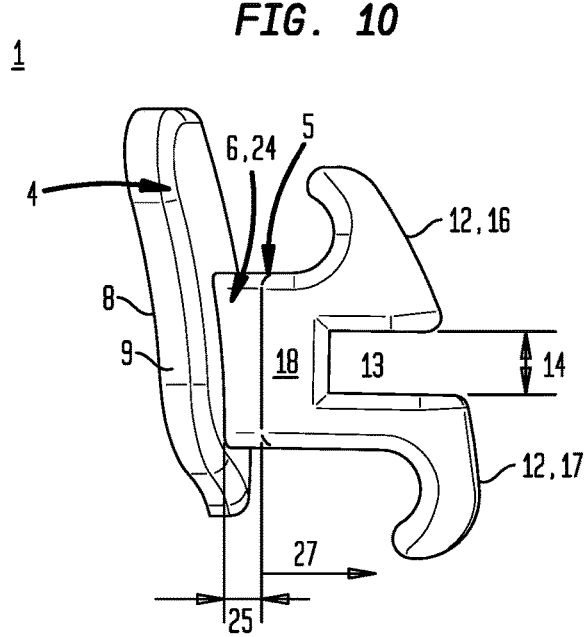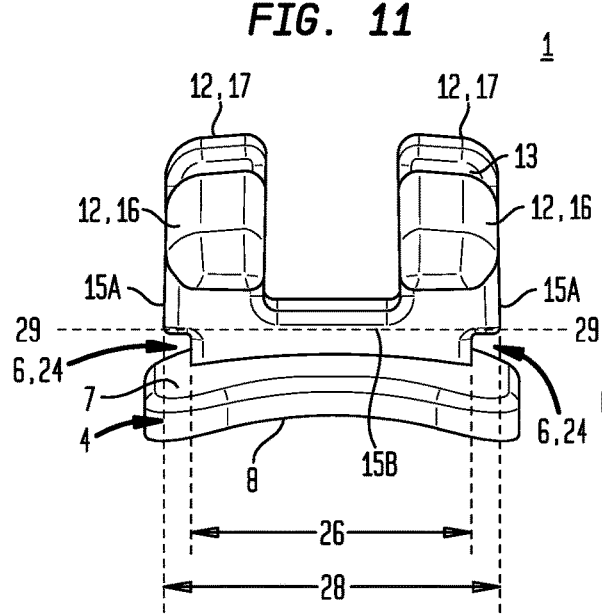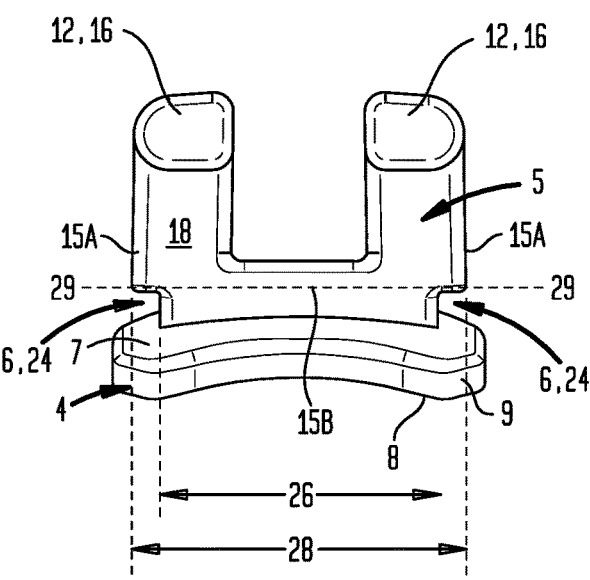

ORTHODONTIC BRACKET RETENTION ANCHOR

I. FIELD OF THE INVENTION

Orthodontic articles such as brackets and methods for the manufacture of brackets having configurations which maintain position or resist movement or displacement during the production of or in the use of bracket placement or transfer apparatuses having a shape that matches the configuration of at least part of the patient's dental arch for use in indirect bonding techniques.

II. BACKGROUND OF THE INVENTION

Orthodontic treatment involves movement of malpositioned teeth to desired locations in the oral cavity. One common type of orthodontic treatment involves the use of small, slotted orthodontic appliances known as brackets. The brackets are fixed to the patient's teeth and an archwire is placed in the slot of each bracket. The archwire forms a track to guide movement of the teeth to desired locations. The ends of orthodontic archwires are often connected to small orthodontic appliances known as buccal tubes that are, in turn, secured to the patient's molar teeth. In many instances, a set of brackets, buccal tubes and an archwire is provided for each of the patient's upper and lower dental arches. The brackets, buccal tubes and archwires are commonly and collectively referred to as "braces".

Orthodontic brackets that are adapted to be adhesively bonded to the patient's teeth can be placed and fixed to the teeth using either one of two techniques known as direct bonding and indirect bonding. Direct bonding techniques generally involve the serial placement of individual adhesive-coated orthodontic brackets onto a patient's tooth surface by an orthodontist. Orthodontic brackets can be manufactured with a layer or coating of orthodontic adhesive on the base of each bracket. Typically, one bracket at a time is placed onto a patient's tooth surface until all of the brackets required for treatment are placed on the teeth. Alternatively, a layer or coating of orthodontic adhesive can be applied to the base of each bracket by the orthodontist immediately before the bracket is placed onto a tooth surface. In direct orthodontic bonding, the layer or coating of orthodontic adhesive on the orthodontic appliance is not hardened until after the orthodontic appliance is placed on a tooth surface. The layer or coating of orthodontic adhesive does not have a contour that is a negative replica of the tooth surface until the adhesive has been placed in contact with the tooth surface. Direct bonding techniques have been used to place and fix a single orthodontic bracket or serially fix a plurality of orthodontic brackets in a patient's oral cavity.

Indirect bonding techniques generally involve the use of a placement device or transfer apparatus having a shape that matches the configuration of at least part of the patient's dental arch. One type of placement device includes a "bonding tray" and typically has a cavity for receiving a plurality of teeth simultaneously. A set of orthodontic brackets may be releasably connected to the bonding tray at certain, predetermined locations. When the tray connected to the orthodontic appliances is placed over the matching portions of the patient's dental arch, each orthodontic appliance can be positioned on the patient's teeth.

In particular conventional indirect bonding techniques, before the bonding tray is formed, the brackets may be fixed to a plurality of teeth of a replica model of the patient's dental arch. Typically, an orthodontic adhesive is applied to the orthodontic brackets, the brackets are pressed onto the replica teeth, and the orthodontic adhesive can cure to a fully hardened condition which may involve use of, an orthodontic curing light. This fully hardened orthodontic adhesive may remain on the orthodontic brackets when it is removed from the replica teeth and can serve as a "custom base" for bonding the brackets to the patient's teeth.

Methods of making indirect bonding trays by taking a negative impression of each of the patient's dental arches and then making a replica model from each negative impression have been largely replaced by three-dimensional scanning or imaging using optical technologies such as: confocal laser microscopy, active wavefront sampling, accordion fringe inferometry, and optical coherent tomography. This may be followed by the use of three-dimensional printing technologies to produce a replica model of the patient's dental arches, such as: fused deposition modeling and printing, selective laser melting or sintering, electron beam melting, or inkjet three-dimensional printing. The brackets may then be temporarily bonded to the three dimensionally printed replica model of the patient's dental arches.

In one conventional example in the production of the bonding tray, a first matrix material can be applied to the orthodontic brackets bonded to the replica model of the patient's dental arches. Preferably, the first matrix material contacts the occlusal, facial, gingival, mesial and distal sides of the brackets. Optionally, but not necessarily, a portion of the first matrix material also contacts sections of the facial sides of the replica teeth of the replica model that extend along the bracket bases. Preferably, the first matrix material has a relatively low viscosity before hardening to assure intimate contact between the first matrix material and each bracket. In this manner, the first matrix material can substantially penetrate in the various recesses, cavities and other structural feature of the plurality of brackets to establish a connection between the first matrix material and each of the plurality of brackets.

An example of a suitable first matrix material may be EMILUMA® brand silicone material from Shofu Dental Corporation. The first matrix material may have a viscosity before curing that is preferably less than about 80,000 centipoise ("cP"), more preferably less than about 25,000 cP and most preferably less than about 8,000 cP. Once hardened, the matrix material may have a tensile stress at 20 percent elongation (according to ASTM D 412) in the range of about 31,000 to about 496,000 Pascal ("Pa"), more preferably in the range of about 62,000 to about 248,000 Pa and most preferably in the range of about 112,000 to about 136,000 Pa, and has a tensile stress at 50 percent elongation that may be in the range of about 91,000 to about 1,460,000 Pa, more preferably in the range of about 183,000 to about 730,000 Pa and most preferably in the range of about 329,000 to about 402,000 Pa. An example of a suitable first matrix material would be a first matrix material having a tensile stress at 20 percent elongation of about 124,000 Pa and a tensile stress at 50 elongation of about 365,000 Pa.

Subsequently, a quantity of a second matrix material may be dispensed to contact the labial, occlusal and lingual surfaces of the replica teeth of the replica model, except in areas covered by the first matrix material. The second matrix material extends over and preferably completely surrounds the first matrix material. Optionally, the second matrix material extends over the distal ends of the first matrix material adjacent the model molar teeth. The second matrix material also preferably surrounds an occlusal stop member except for those regions of the occlusal stop member that are in contact with the arch model. In this embodiment, the occlusal stop member is spaced from the first matrix material and separated from the first matrix material by the second matrix material.

An example of a suitable second matrix material is MEMOSIL 2® brand vinyl polysiloxane material from Heraeus Kulzer, Inc. The second matrix material can have a viscosity before hardening that is preferably less than about 1,000,000 cP, more preferably less than about 100,000 cP and most preferably less than about 8,000 cP. Once hardened, the second matrix material has a tensile stress at 20 percent elongation (according to ASTM D 412) that may be in the range of about $0.4 \times 10^6$ Pa to about $6.5 \times 10^6$ Pascal, more preferably in the range of about $0.8 \times 10^6$ Pa to about $3.3 \times 10^6$ Pa and most preferably in the range of about $1.1 \times 10^6$ Pa to about $1.4 \times 10^6$ Pa, and may have a tensile stress at 50 percent elongation that is in the range of about $0.8 \times 10^6$ Pa to about $12.5 \times 10^6$ Pa, more preferably in the range of about $1.6 \times 10^6$ to about $6.2 \times 10^6$ Pa and most preferably in the range of about $2.8 \times 10^6$ Pa to about $3.4 \times 10^6$ Pa. An example of a suitable second matrix material would be a second matrix material having a tensile stress at 20 percent elongation of about $1.3 \times 10^6$ Pa and a tensile stress at 50 elongation of about $3.1 \times 10^6$ Pa.

In methods which employ a second matrix material, the second matrix material can have a composition that is different than the composition of the first matrix material, and after hardening exhibits a tensile stress at 20 percent elongation that is preferably greater than the tensile stress at 20 percent elongation that is exhibited by the first matrix material after hardening. Preferably, the second matrix material chemically bonds to the first matrix material with a relatively high bond strength.

A bonding tray may further include an occlusal stop member that is connected to the second matrix material. Because the occlusal stop member matches the shape of the corresponding cusp tips of the replica teeth, the occlusal stop member can be firmly seated on the arch model in such a manner that little, if any, relative lateral movement is possible between the occlusal stop member and the arch model in an occlusal reference plane. The mated relation of the bonding tray to the teeth also helps to reduce the amount of unintended lateral movement of the tray before such time as the appliances are firmly bonded to the patient's teeth.

The occlusal stop member may be relatively inflexible having a Shore A hardness that is greater than the Shore A hardness of either of the first matrix material or the second matrix material. Preferably, the occlusal stop member has a Shore A hardness that is greater than about 72, more preferably has a Shore A hardness that is greater than about 90, even more preferably has a Shore D hardness that is greater than about 60 and most preferably has a Shore D hardness that is greater than about 75. An example of a suitable hardness is 72 Shore A hardness.

A bonding tray, including the brackets, connected to at least one matrix material, and optionally a second matrix material and the occlusal stop member thus formed, can then be removed from the replica model. Excess material of the tray may be trimmed as desired before use.

Other methods in production of the bonding tray may avoid use of the replica model of the patient's dental arches. A virtual replica model may be generated by three-dimensional scanning or imaging data of the patient's dental arch. One or a plurality of brackets can be virtually positioned in correct orientations relative to the virtual replica model. An indirect bonding tray may then be produced by three-dimensional printing using one or more matrix materials. The three dimensionally printed bonding tray includes negative spaces disposed in correct orientations to correspondingly receive and correctly orient one or a plurality of brackets. In this method, only one matrix material may be used in production of the bonding tray. The matrix material used in the three-dimensional printing of bonding trays, when cured, may have a wide range of Shore A hardness. The Shore A hardness can be between about 50 to about 90 with a tensile strength of between about $1.0 \times 10^6$ Pa to about $5.0 \times 10^6$ Pa.

Regardless of the method used to produce the bonding tray, the patient's teeth that are to receive the brackets may be dried, treated with an etching solution and a bonding adhesive can be applied to the bonding pad of the brackets retained in the bonding tray or to selected areas of the patient's teeth. The bonding tray retaining the brackets can then be positioned over the corresponding teeth of the patient and seated. Since the shape of the cavity presented by the matrix material(s), and optionally the occlusal stop member, together match the shape of the underlying teeth, the plurality of brackets can be concurrently seated against the underlying teeth with the intention of matching the same locations corresponding to the previous respective positions of the plurality of teeth on the replica model or at which the brackets were mechanically disposed based on three dimensional imaging data. Once the bonding adhesive has hardened, the bonding tray can be carefully removed from the patient's dental arch. After the bonding tray has been released from the patient's dental arch, an archwire is placed in the archwire slots of the brackets and ligated in place.

Understandably, the precise position of the brackets within the bonding tray at the time the bonding tray concurrently seats the plurality of brackets against the corresponding plurality of underlying teeth is an important factor to ensure that the teeth move to their intended final positions. However, counterpoised to maintaining the position of the brackets within the bonding tray at these precise locations, the matrix material must be relatively soft to readily release from the plurality of brackets correspondingly bonded to the plurality of teeth in the dental arch. The first matrix material can therefore allow one or more of the brackets to reposition within or prematurely release from the bonding tray during release from the replica model or during bonding to the patient's teeth.

Accordingly, there would an advantage in a bracket having a configuration which resisted repositioning or premature release from the matrix material during production, release from the replica model, or during bonding to the patient's teeth.

III. SUMMARY OF THE INVENTION

A broad object of the present invention can be to provide a bracket having a configuration to resist movement in a matrix material of a bonding tray. The bracket can include one or more of a bracket base, a bracket body secured to the bracket base, and a bracket retention anchor disposed on the bracket body surface to assist in anchoring the bracket to the matrix material of the bonding tray.

Another broad object of the invention can be to provide a method of anchoring brackets in a bonding tray including one or more of obtaining a plurality of brackets each including one or more of a bracket base, a bracket body secured to the bracket base, and a bracket retention anchor disposed on the bracket body surface to assist in anchoring the bracket to a matrix material. The method can further include one or more of obtaining a replica model of a plurality of teeth of a dental arch, releasably bonding the plurality of brackets on the replica model at the locations or in the orientations corresponding to the locations or orientations on the teeth of the patient when fixedly seated, applying a matrix material to the plurality of brackets and permitting the matrix material to cure. The method can further include releasing the plurality of brackets from the replica model, and removing the matrix material from a replica model.

Another broad object of the invention can be to provide a method of anchoring brackets in a bonding tray including one or more of obtaining a plurality of brackets each including one or more of a bracket base, a bracket body secured to the bracket base, and a bracket retention anchor disposed on the bracket body surface to assist in anchoring the bracket to a matrix material. The method can further include one or more of obtaining a virtual replica model of a plurality of teeth of a dental arch, producing a bonding tray based on the virtual replica model of the plurality of teeth of the dental arch including one or a plurality of cavities configured to correspondingly receive one or more brackets, each of the one or plurality of cavities having cavity walls configured to correspondingly mating engage the bracket retention anchor disposed on the bracket body to retain the one or the plurality of brackets in the bonding tray at the locations or in the orientations corresponding to the locations or orientations on the teeth of the patient when fixedly seated, correspondingly disposing the one or plurality of brackets in the one or more cavities of the bonding tray with mated engagement of the cavity walls with the bracket retention anchor.

Naturally, further objects of the invention are disclosed throughout other areas of the specification, drawings, photographs, and claims.

IV. BRIEF DESCRIPTION OF THE DRAWINGS

FIG. 10 is a side elevation view of a particular embodiment of a bracket including a bracket retention anchor.

FIG. 11 is a front elevation view of a particular embodiment of a bracket including a bracket retention anchor.

FIG. 12 is a back elevation view of a particular embodiment of a bracket including a bracket retention anchor.

V. DETAILED DESCRIPTION OF THE INVENTION

Figure 1:
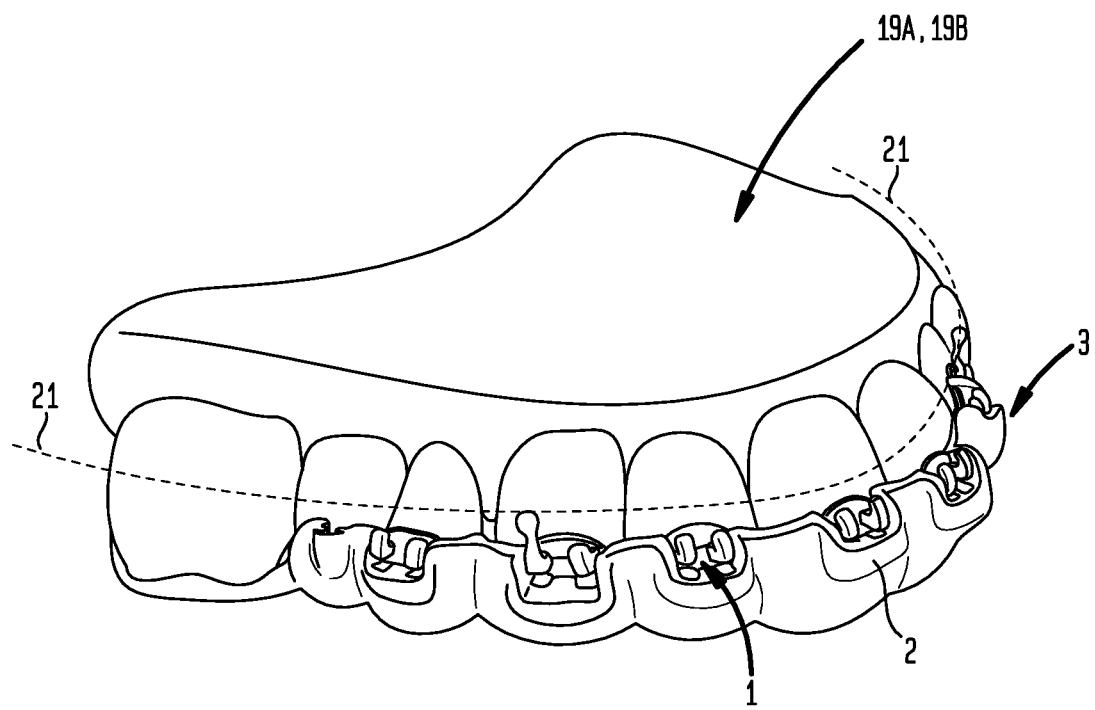
FIG. 1 is a perspective view of a particular embodiment of a bonding tray connected to bracket retention anchors of a corresponding plurality of brackets positioned on a replica model of a patient's dental arch.

In general, a bracket (1) having a configuration which resists movement in a matrix material (2) of a bonding tray (3). The bracket (1) can include a bracket base (4), a bracket body (5), and a bracket retention anchor (6). The bracket base (4) can have a top surface (7) and a bottom surface (8) joined at a peripheral edge (9). The bracket body (5) can have a bracket body first end (10) secured to the top surface (7) of the bracket base (4) and a bracket body second end (11) which terminates in a plurality of bracket heads (12) disposed a distance apart defining an archwire slot (13). In particular embodiments, the bracket body (5) can, but need not necessarily have two pairs of opposed bracket sides (15A)(15B). Each pair of opposed bracket sides (15A)(15B) can include a pair of bracket heads (12), the pair of bracket heads (12) including a top bracket head (16) and a bottom bracket head (17) disposed about the archwire slot (13). The bracket retention anchor (6) can be disposed on the bracket body surface (18) between the bracket body first end (10) and the bracket body second end (11). The bracket retention anchor (6) can be configured to assist in anchoring the bracket (1) to the matrix material (2) of a bonding tray (3).

For purposes of this invention, the term "anchoring" means holding a bracket (1) in a substantially fixed position of a bonding tray (3) in response to forces exerted on the bracket (1) during normal production or use of the bonding tray (3). The bracket material can be any one or a combination of rigid materials, such as: a metal, a plastic, a ceramic, or other like rigid material.

Referring generally to FIGS. 1 through 6, particular methods of anchoring brackets (1) in a bonding tray (3) can include obtaining a replica model (19) of a plurality of teeth (20) of a dental arch (21), obtaining a plurality of brackets (1), each including a bracket base (4), a bracket body (5), and a bracket retention anchor (6), releasably bonding the plurality of brackets (1) at locations on the replica model (19) of the plurality of teeth (20) of the dental arch (21), applying a matrix material (2) to the plurality of brackets (1), releasing the plurality of brackets (1) from the replica model (19) of the plurality of teeth (20) of the dental arch (21), and removing the matrix material (2) from the replica model (19) of the dental arch (21). In applying the matrix material (2) to the plurality of brackets (1) releasably bonded to the replica model (19) of the plurality of teeth (20) in the dental arch (21), the matrix material (2) can contact the bracket retention anchor (6) of each of the plurality of brackets (1). The matrix material (2) can further be curable to establish a connection between the matrix material (2) and the bracket retention anchor (6). The connection between the matrix material (2) and the bracket retention anchor (6) can maintain the position of each of the plurality of brackets (1) in the matrix material (2).

Now referring primarily to FIGS. 3 through 6, particular methods of anchoring brackets (1) in a bonding tray (3) can include obtaining a plurality of brackets (1) each including one or more of a bracket base (4), a bracket body (5) secured to the bracket base (4), and a bracket retention anchor (6) disposed on the bracket body surface (18) to assist in anchoring the bracket (1) to a matrix material (22A) of the bonding tray (3). A virtual replica model (19B) of the dental arch (21) of the patient (P) may be generated by three-dimensional scanning or imaging data of the patient's (P) dental arch (21). One or a plurality of brackets (1) can be virtually positioned in correct orientations relative to the virtual replica model (19B). An indirect bonding tray (3) can then be produced by three-dimensional printing (or other three-dimensional forming or fabrication process) using one or more matrix materials (22A). The printed, formed or fabricated indirect bonding tray (3) can include one or a plurality of cavities (22C) configured to correspondingly receive one or more of brackets (1). In producing the bonding tray (3), each of the one or plurality of cavities (22C) can have cavity walls (22D) configured to correspondingly mating engage the bracket retention anchor (6) of the bracket body (5). Mated engagement of the cavity walls (22D) with the bracket retention anchor (6) assists in retaining the one or the plurality of brackets (1) in the bonding tray (3) at the locations or in the orientations corresponding to the locations or orientations on the teeth (22) of the patient (P) when the bonding tray (3) is used to transfer and fixedly seat the one or plurality of brackets (1) to the teeth (22) of the patient (P), correspondingly disposing the one or plurality of brackets (1) in the one or more cavities (22C) of the bonding tray (3) with mated engagement of the cavity walls (22D) with the bracket retention anchor (6). Now referring to primarily to FIG. 2B, the term "mated engagement" for the purposes of this invention means that the cavity walls (22C) include one or more bracket retention anchor mating features (22E) having a structure and location which conformably mates with the structure of the bracket retention anchor (6) on the bracket body (5) to retentively fix the location and orientation of the one or plurality of brackets (1) in the bonding tray (3).

The matrix material (2) can include a first matrix material (22A). In particular embodiments, the first matrix material (22A), before curing, can have a viscosity of about 8,000 cP to about 80,000 cP. In particular embodiments, the viscosity of the first matrix material (48) before curing can be selected from the group including: about 10,000 cP to about 20,000 cP, about 15,000 cP to about 25,000 cP, about 20,000 cP to about 30,000 cP, about 25,000 cP to about 35,000 cP, about 30,000 cP to about 40,000 cP, about 35,000 cP to about 45,000 cP, about 40,000 cP to about 50,000 cP, about 45,000 cP to about 55,000 cP, about 50,000 cP to about 60,000 cP, about 55,000 cP to about 65,000 cP, about 60,000 cP to about 70,000 cP, about 65,000 cP to about 75,000 cP, or combinations thereof.

The first matrix material (22A) can be cured to establish a tensile strength at 20 percent elongation ASTM D 412 of about 31,000 Pa to about 496,000 Pa. In particular embodiments, the tensile strength at 20 percent elongation ASTM D 412 of the cured first matrix material (22) can be selected from the group including: about 50,000 Pa to about 150,000 Pa, about 100,000 Pa to about 200,000 Pa, about 150,000 Pa to about 250,000 Pa, about 200,000 Pa to about 300,000 Pa, about 250,000 Pa to about 350,000 Pa, about 300,000 Pa to about 400,000 Pa, about 350,000 Pa to about 450,000 Pa, or combinations thereof. The first matrix material (22A) can further be cured to establish a tensile stress at 50 percent elongation ASTM D 412 of about 91,000 Pa to about 1,460,000 Pa. The tensile stress at 50 percent elongation ASTM D 412 of the cured first matrix material (22A) can be selected from the group including: about 100,000 Pa to about 300,000 Pa, about 200,000 Pa to about 400,000 Pa, about 300,000 Pa to about 500,000 Pa, about 400,000 Pa to about 600,000 Pa, about 500,000 Pa to about 700,000 Pa, about 600,000 Pa to about 800,000 Pa, about 700,000 Pa to about 900,000 Pa, about 800,000 Pa to about 1,000,000 Pa, about 900,000 Pa to about 1,100,000 Pa, about 1,000,000 Pa to about 1,200,000 Pa, about 1,100,000 Pa to about 1,300,000 Pa, about 1,200,000 Pa to about 1,400,000 Pa, or combinations thereof.

Figure 2A:
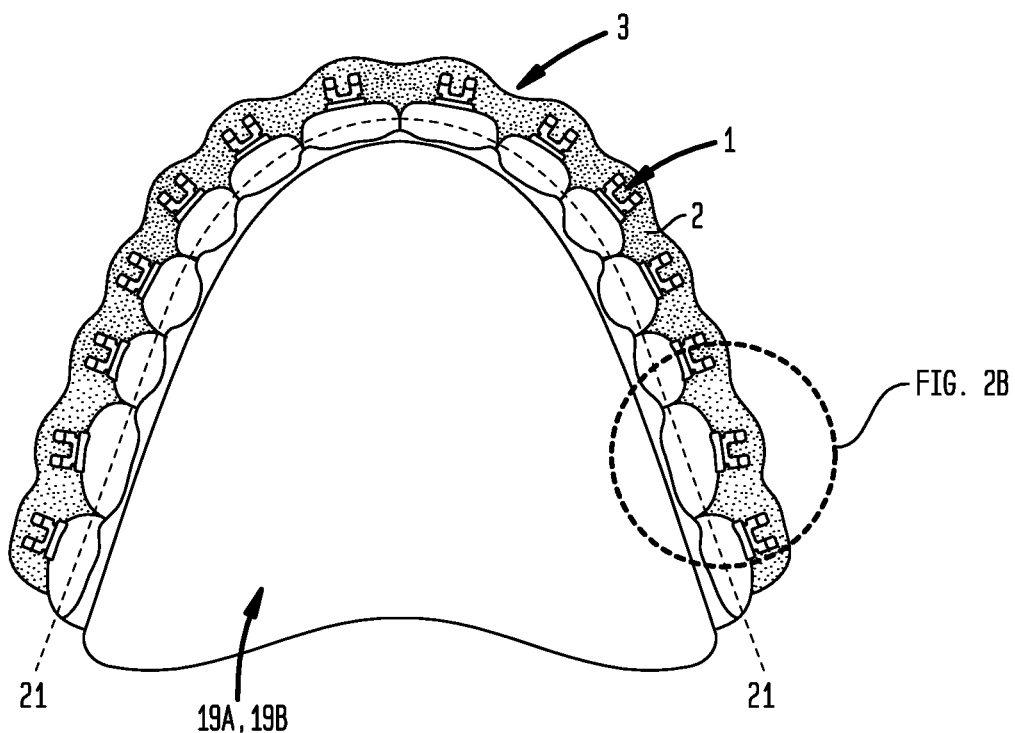
FIG. 2A is a bottom plan view of a particular embodiment of a bonding tray connected to bracket retention anchors of a corresponding plurality of brackets positioned on a replica model.
Figure 2B:
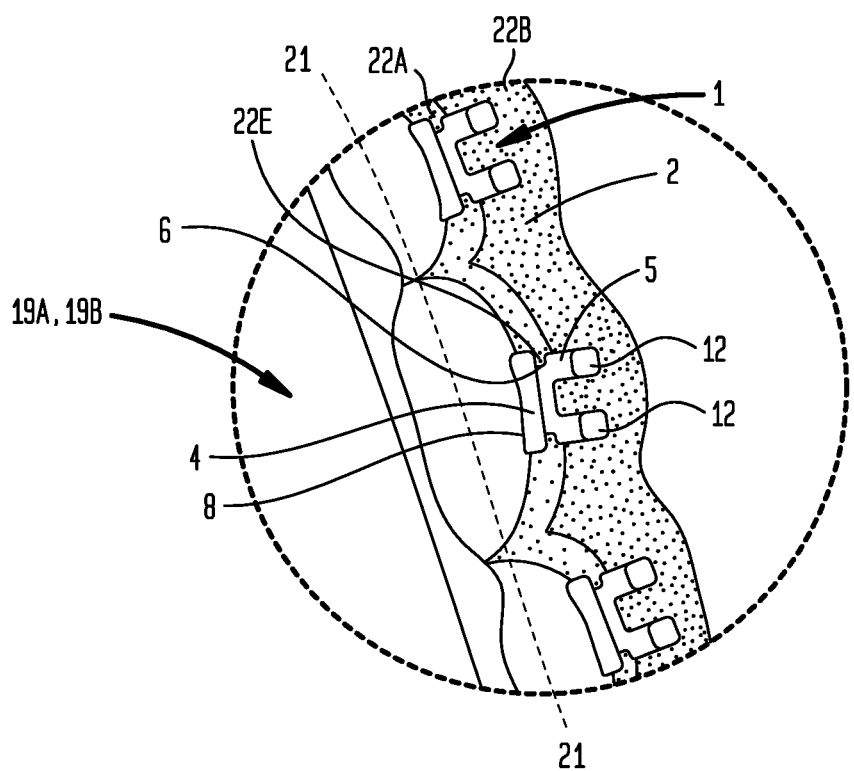
FIG. 2B is an enlargement of the particular embodiment of FIG. 2A showing brackets anchored in a bonding tray positioned on a replica model.
Figure 2C:
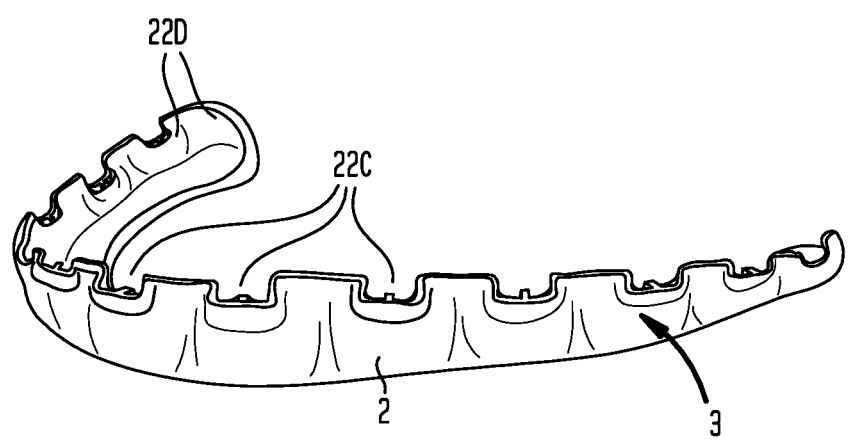
FIG. 2C is a perspective view of a particular embodiment of a bonding tray.
Figure 3:
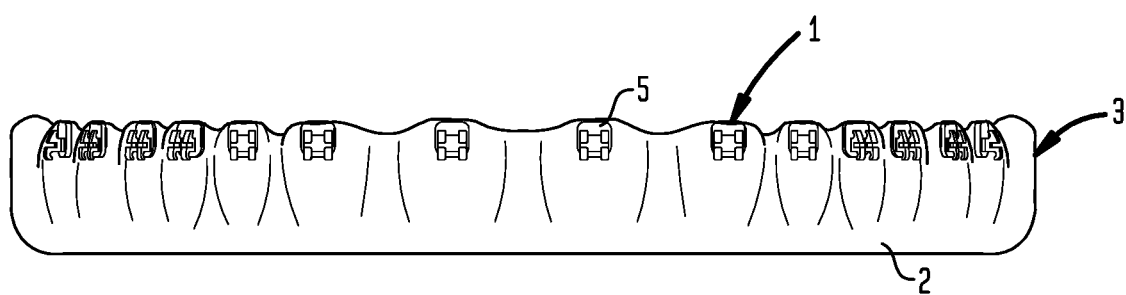
FIG. 3 is a front elevation view of a particular embodiment of a bonding tray having a plurality of brackets including bracket retention anchors connected to the matrix material of the bonding tray.
Figure 4:
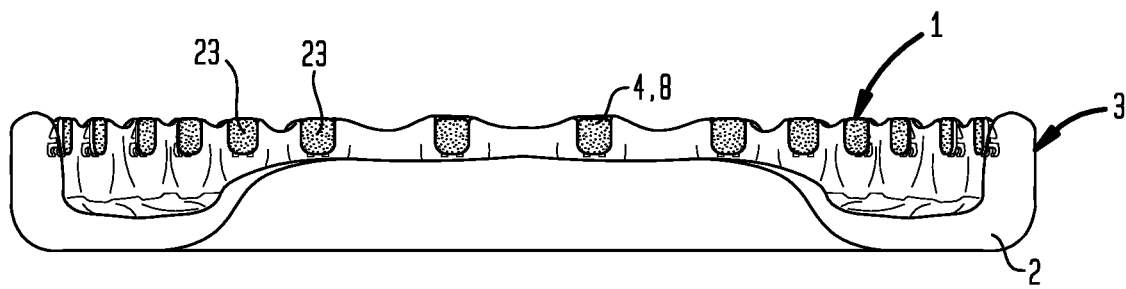
FIG. 4 is a rear elevation view of a particular embodiment of a bonding tray with brackets as shown in FIG. 3.
Figure 5:
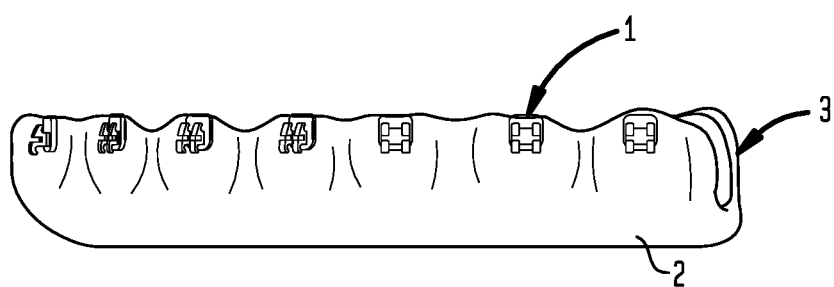
FIG. 5 is a side elevation view of a particular embodiment of a bonding tray with brackets as shown in FIG. 3.
Figure 6:
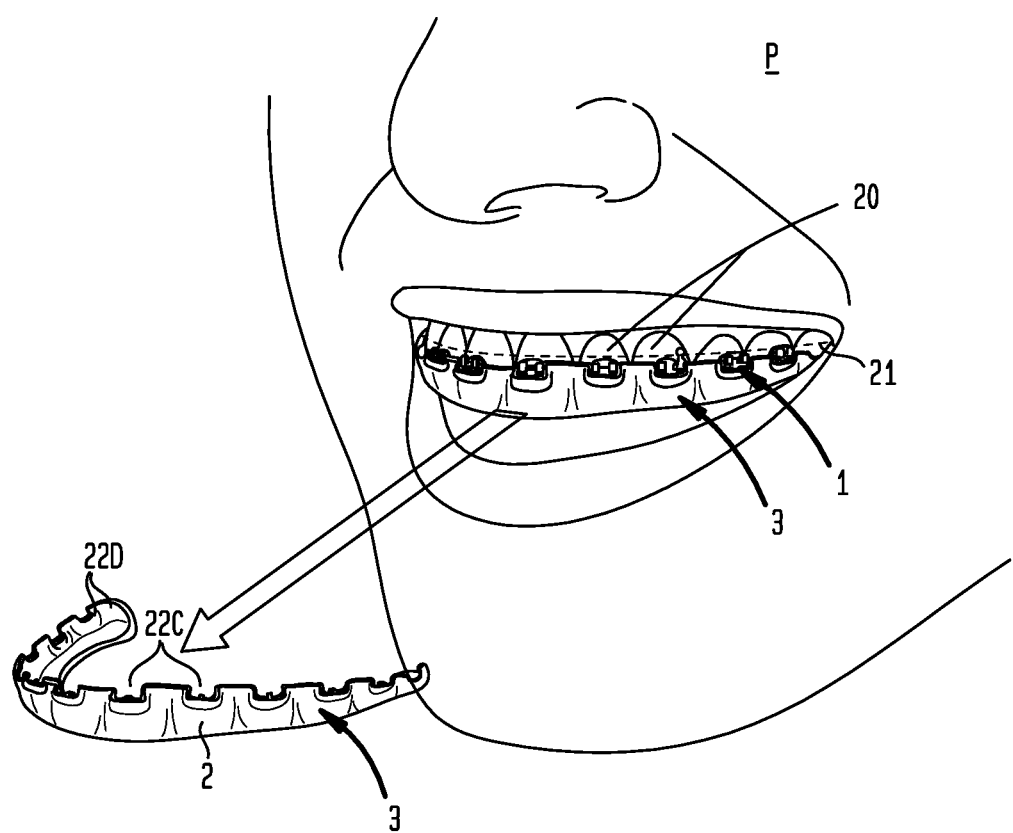
FIG. 6 is a perspective view of a particular method of using a bonding tray to dispose brackets on a patient's dental arch and removal of the bonding tray from the brackets.
Figure 7:
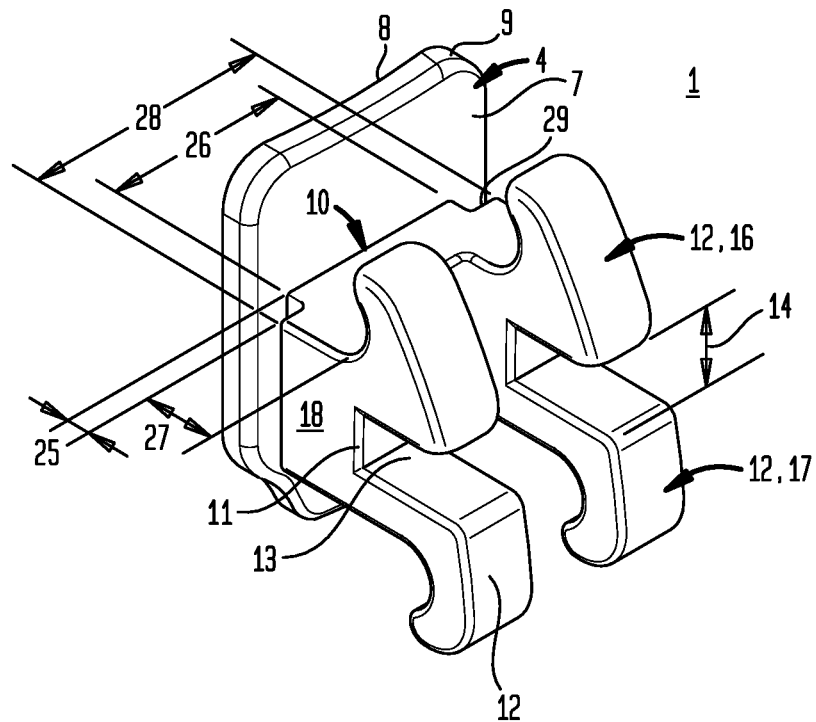
FIG. 7 is a perspective view of a particular embodiment of a bracket including a bracket retention anchor.
Figure 8:
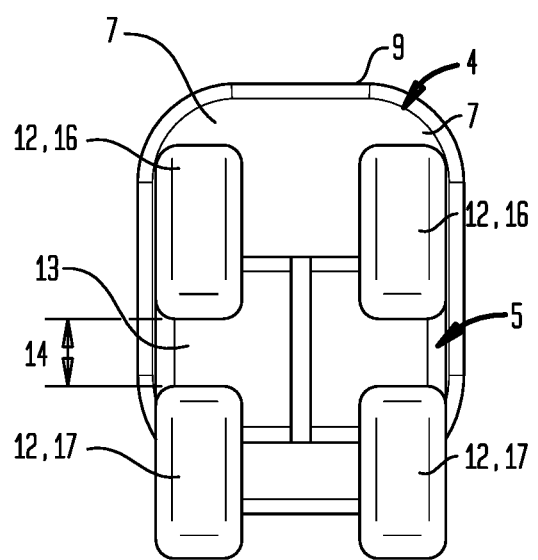
FIG. 8 is a top plan view of a particular embodiment of a bracket including a bracket retention anchor.
Figure 9:
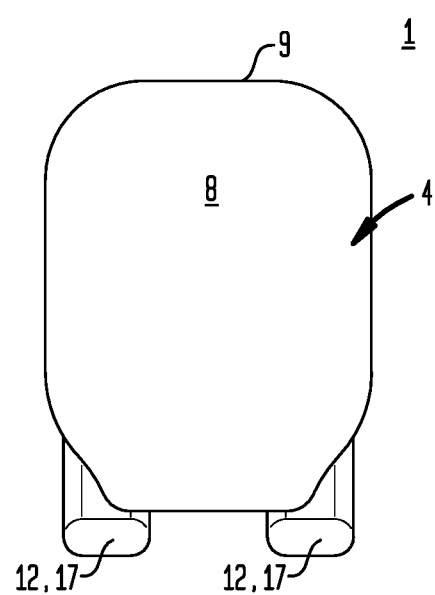
FIG. 9 is a bottom plan view of a particular embodiment of a bracket including a bracket retention anchor.

Now referring primarily to FIG. 2B, in particular embodiments, the bonding tray (3) may be produced entirely from only one matrix material (2) (such as the first matrix material (22A) above described). In particular embodiments, the matrix material (2) can, but need not necessarily, include a first matrix material (22A) and a second matrix material (22B). As an illustrative example, the second matrix material (22B) can, but need not necessarily, be a different composition than the first matrix material (22A). The second matrix material (22B) can be applied to the replica model (19) of the plurality of teeth (20) of the dental arch (21) after curing the first matrix material (22A). The second matrix material (22B) can extend over the first matrix material (22A). The second matrix material can be curable to bond the second matrix material (22B) to the first matrix material (22A) disposed on the bracket (1).

The second matrix material (22B) can have a viscosity, before curing, of about 8,000 cP to about 1,000,000 cP. The viscosity of the second matrix material can be selected from the group including: about 10,000 cP to about 100,000 cP, about 50,000 cP to about 150,000 cP, about 100,000 cP to about 200,000 cP, about 150,000 cP to about 250,000 cP, about 200,000 cP to about 300,000 cP, about 250,000 cP to about 350,000 cP, about 300,000 cP to about 400,000 cP, about 350,000 cP to about 450,000 cP, about 400,000 cP to about 500,000 cP, about 450,000 cP to about 550,000 cP, about 500,000 cP to about 600,000 cP, about 550,000 cP to about 650,000 cP, about 600,000 cP to about 700,000 cP, about 650,000 cP to about 750,000 cP, about 700,000 cP to about 800,000 cP, about 750,000 cP to about 850,000 cP, about 800,000 cP to about 900,000 cP, about 850,000 cP to about 950,000 cP, or combinations thereof.

After curing the second matrix material (22B), the second matrix material (22B) can have a tensile strength at 20 percent elongation ASTM D 412 greater than the tensile stress at 20 percent elongation ASTM D 412 of the first matrix material (22A) after the first matrix material (22A) cures. Further, the second matrix material (22B) can be cured to establish a tensile stress at 50 percent elongation ASTM D 412 of about 800,000 Pa to about 12,500,000 Pa. The tensile stress at 50 percent elongation ASTM D 412 of the cured second matrix material can be selected from the group including: about 1,000,000 Pa to about 2,000,000 Pa, about 1,500,000 Pa to about 2,500,000 Pa, about 2,000,000 Pa to about 3,000,000 Pa, about 2,500,000 Pa to about 3,500,000 Pa, about 3,000,000 Pa to about 4,000,000 Pa, about 3,500,000 Pa to about 4,500,000 Pa, about 4,000,000 Pa to about 5,000,000 Pa, about 4,500,000 Pa to about 5,500,000 Pa, about 5,000,000 Pa to about 6,000,000 Pa, about 5,500,000 Pa to about 6,500,000 Pa, about 6,000,000 Pa to about 7,000,000 Pa, about 6,500,000 Pa to about 7,500,000 Pa, about 7,000,000 Pa to about 8,000,000 Pa, about 7,500,000 Pa to about 8,500,000 Pa, about 8,000,000 Pa to about 9,000,000 Pa, about 8,500,000 Pa to about 9,500,000 Pa, about 9,000,000 Pa to about 10,000,000 Pa, about 9,500,000 Pa to about 10,500,000 Pa, about 10,000,000 Pa to about 11,000,000 Pa, about 10,500,000 Pa to about 11,500,000 Pa, about 11,000,000 Pa to about 12,000,000 Pa, or combinations thereof.

As to particular embodiments, the matrix material(s)(22) used in the three-dimensional printing (or other forming or fabrication process) of the bonding trays (3), when cured, may have Shore A hardness which falls in a wide range of Shore A hardnesses. The Shore A hardness can, as an example, be between about 50 to about 90. Similarly, the tensile strength of the matrix material (22) can be between about $1.0 \times 10^6$ Pa to about $5.0 \times 10^6$ Pa. However, the above illustrative Shore A hardness or tensile strength is not intended to preclude embodiments which fall outside of these ranges.

Now referring primarily to FIGS. 3 through 6, methods can further include applying a bonding material (23) to the bottom surface (8) of the bracket base (4) of each of the plurality of brackets (1) retained in the matrix material (2), positioning the bonding tray (3) (which retains the one or plurality of brackets (1)) to the plurality of teeth (20) of the dental arch (21), and concurrently seating the plurality of brackets (1) to the plurality of teeth (20) in the dental arch (21). The seating of the plurality of brackets (1) to the plurality of teeth (20) in the dental arch (21) can substantially correspond to the locations at which the plurality of brackets (1) were releasably bonded on the replica model (19) or virtually positioned in the virtual replica model (19B). The precise location or orientation of the brackets (1) in the matrix material (2) can be maintained based on the connection or mated engagement between the matrix material (2), (22A) and each of the bracket retention anchors (6) disposed on the plurality of brackets (1).

Particular methods of anchoring brackets (1) in a bonding tray (3) can further include increasing the precision of matching the location at which one or more of the plurality of brackets (1) with the bracket retention anchors (6) connected to the matrix material (2) seat on the plurality of teeth (20) in the dental arch (21) to corresponding locations where the plurality of brackets (1) were releasably bonded on the replica model (19) of the teeth of the dental arch (21) or virtually positioned on the virtual replica model (19B). The increase in precision can be attributed to bracket retention anchors (6) connected or mateably engaged to the matrix material (2), and can be measured in comparison to the precision of matching the location at which one or more of the plurality of brackets (1) without the bracket retention anchors (6) connected to the matrix material (2) seat on the plurality of teeth (20) in the dental arch (21) to the corresponding locations where the plurality of brackets (1), without the bracket retention anchors (6), were releasably bonded on the replica model (19) of the teeth of the dental arch (21) or positioned in the virtual replica model (19B) of the plurality of teeth (20) of the dental arch (21).

Now referring generally to FIGS. 7 through 14B and 16A through 18B, particular embodiments of the bracket retention anchor (6) can include a recess element (24). The recess element (24) can be disposed in the bracket body surface (18) between the bracket body first end (10) and the bracket body second end (11). The matrix material (2)(or the first matrix material 22A) of the bonding tray (3) can be disposed in the recess element (24) to assist in anchoring the bracket (1) in the matrix material (2) of the bonding tray (3).

Now referring generally to FIGS. 7 through 12, particular embodiments of the recess element (24) can define a first portion (25) of the bracket body (5) proximate the bracket base (4) having a first width (26). The recess element (24) can also define a second portion (27) of the bracket body (5) distal to the bracket base (4) having a second width (28). The second width (28) can be greater than the first width (26)(as shown in the illustrative example of FIG. 7). The first portion (25) of the bracket body (5) can further be defined as that portion of the bracket body (5) located between the bracket body first end (10) and the boundary (29), where the boundary (29) comprises the planar intersection of the first portion (25) and the second portion (27) wherein the first width (26) and the second width (28) are collinear. The second portion (27) of the bracket body (5) can further be defined as that portion of the bracket body (5) located between the boundary and the bracket body second end (11) (as shown in the illustrative example of FIG. 7).

Figure 13A:
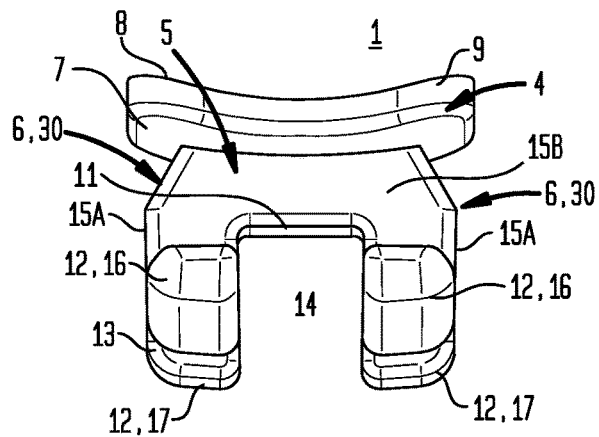
FIG. 13A is a front elevation view of another particular embodiment of a bracket including a bracket retention anchor.
Figure 13B:
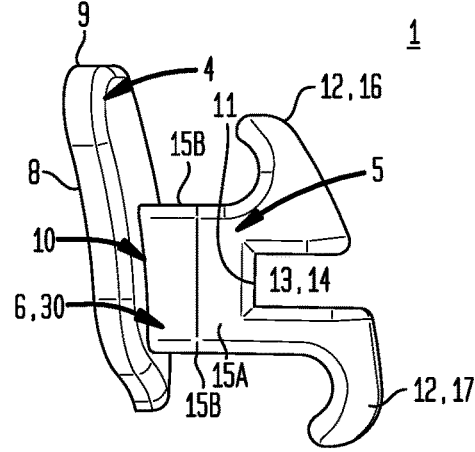
FIG. 13B is a side elevation view of another particular embodiment of a bracket including a bracket retention anchor.

Now referring generally to FIGS. 13A and 13B, particular embodiments of the bracket retention anchor (6) can include a taper element (30). In such embodiments, at least one of the bracket body surfaces (18) can taper approaching the bracket body first end (10). The matrix material (2) of the bonding tray (3) can be disposed about the taper element (29) to assist in positional anchoring of the bracket (1) in the matrix material (2) of the bonding tray (3). In embodiments having two pairs of opposed bracket sides (15A)(15B), each of a first pair of the two pairs of the opposed bracket sides (15A) can taper approaching the bracket body first end (10) (as shown in the illustrative example of 15A). In further particular embodiments, each of the two pairs of opposed bracket sides (15A)(15B) can taper approaching the bracket body first end (10). Further, the taper element (29) can occur proximate the bracket body first end (10)(for example occurring in less than one half the distance between bracket top surface (7) and the archwire slot (13).

Figure 14A:
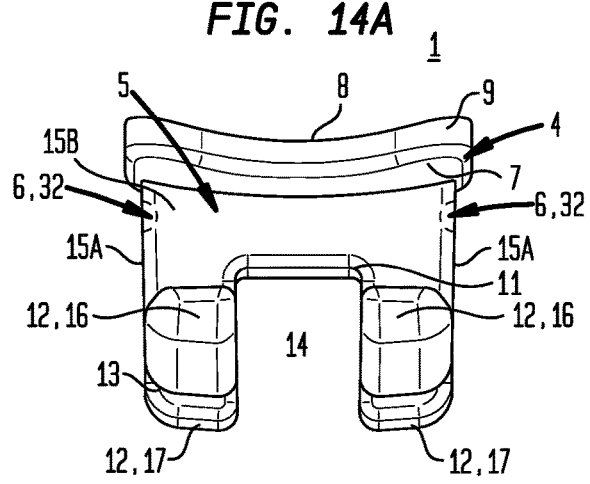
FIG. 14A is a front elevation view of another particular embodiment of a bracket including a bracket retention anchor.
Figure 14B:
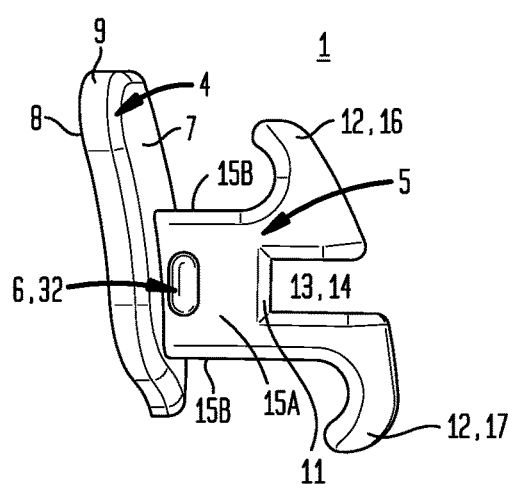
FIG. 14B is a side elevation view of another particular embodiment of a bracket including a bracket retention anchor.

Now referring generally to FIGS. 14A and 14B, embodiments of the recess element (24) can include one or more indentations (32) disposed in the bracket body surface (18). The one or more indentations (32) can, but need not necessarily, include or consist of a concave hemisphere, concave cube or other concave indentation (32).

Figure 15A:
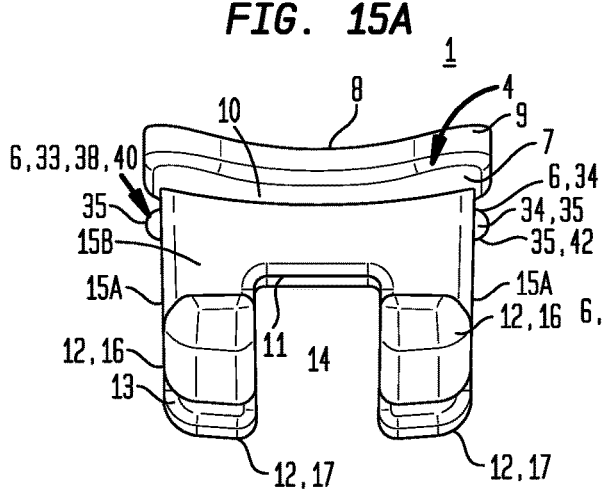
FIG. 15A is a front elevation view of another particular embodiment of a bracket including a bracket retention anchor.
Figure 15B:
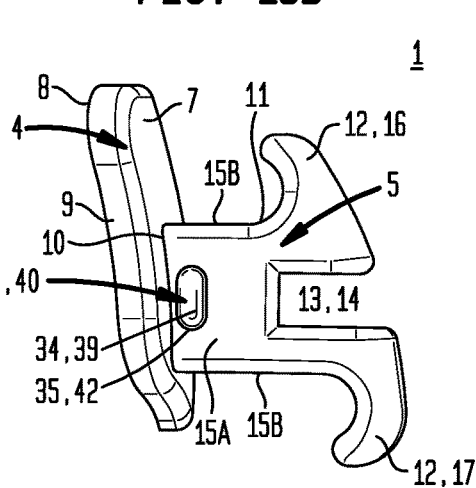
FIG. 15B is a side elevation view of another particular embodiment of a bracket including a bracket retention anchor.
Figure 16A:
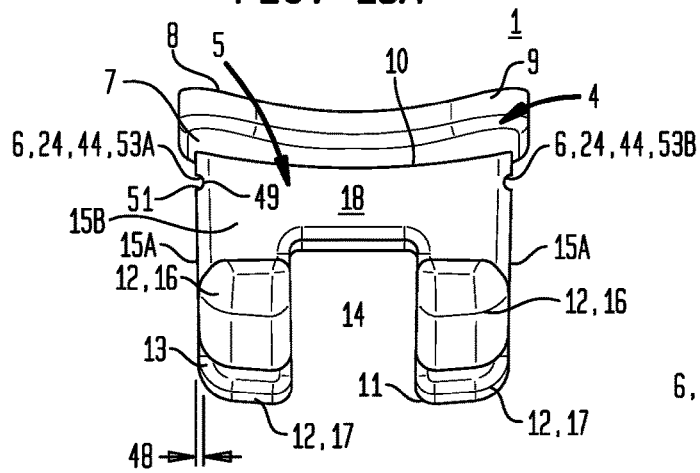
FIG. 16A is a front elevation view of another particular embodiment of a bracket including a bracket retention anchor.
Figure 16B:
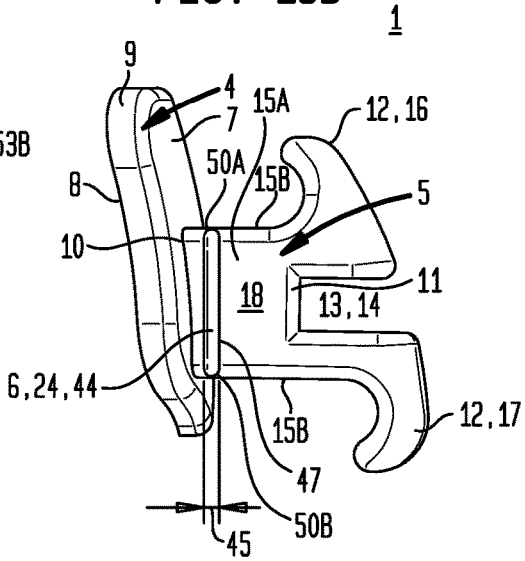
FIG. 16B is a side elevation view of another particular embodiment of a bracket including a bracket retention anchor.
Figure 17A:
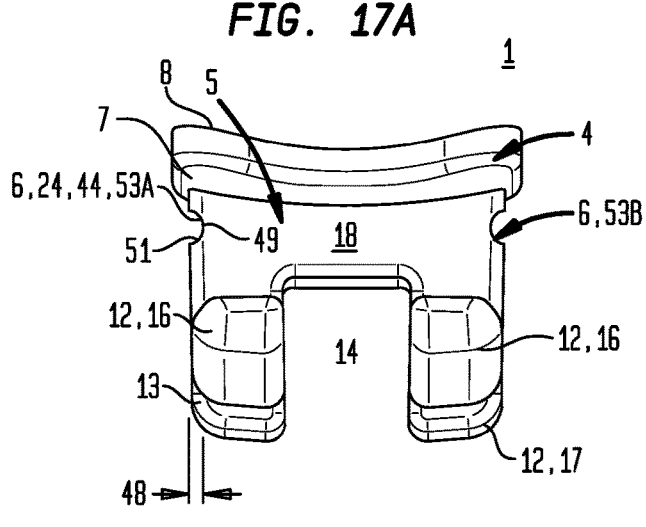
FIG. 17A is a front elevation view of another particular embodiment of a bracket including a bracket retention anchor.
Figure 17B:
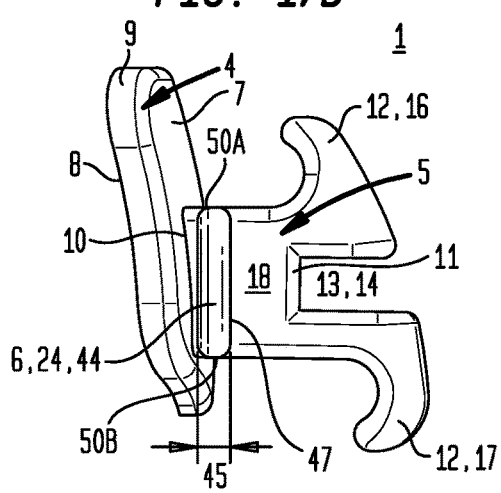
FIG. 17B is a side elevation view of another particular embodiment of a bracket including a bracket retention anchor.

Now referring generally to FIGS. 15A and 15B, particular embodiments of the bracket retention anchor (6) can include a projection element (33). The projection element (33) can extend outward of the bracket body surface (18). The projection element (33) can be disposed between the bracket body first end (10) and the bracket body second end (11). The projection element (33) can, but need not necessarily, be one element extending outward of the bracket body surface (18), such as, a protruding hemisphere, protruding cube or other like protrusion. In other embodiments, the projection element (33) can, but need not necessarily, be a plurality of protruding elements, such as a plurality of hemispheres, a plurality of protruding cubes, or other like protrusions, or combinations thereof. The matrix material (2) of the bonding tray (3) can be disposed about the projection element (33) to assist in the positional anchoring of the bracket (1) in the matrix material (2) of the bonding tray (3).

As shown in the illustrative example of FIGS. 15A and 15B, particular embodiments of the projection element (33) can include a rib (38) disposed on the bracket body surface (18). The rib (38) can have an elongate body (39) disposed between a rib first end (40) and a rib second end (41). The rib (38) can, but need not necessarily, circumferentially extend around the bracket body (5). The rib (38) can be disposed medially on the bracket body (5). In further particular embodiments, the rib (38) can have an orthogonal cross-section to the longitudinal axis of the rib defining a generally arcuate rib surface (42). The arcuate rib surface (42) can define an arc measure of about 45 degrees to about 180 degrees. In particular embodiments, the arc measure can be selected from the group including: about 50 degrees to about 70 degrees, about 60 degrees to about 80 degrees, about 70 degrees to about 90 degrees, about 80 degrees to about 100 degrees, about 90 degrees to about 110 degrees, about 100 degrees to about 120 degrees, about 110 degrees to about 130 degrees, about 120 degrees to about 140 degrees, about 130 degrees to about 150 degrees, about 140 degrees to about 160 degrees, about 150 degrees to about 170 degrees, or combinations thereof.

In particular embodiments of the projection element (33) can further include a pair of ribs. In embodiments of the bracket body (5) having two pairs of opposed bracket sides (15A)(15B), one of each of the pair of ribs (38) can be correspondingly disposed on the first pair (15A) of the two pairs of opposed bracket sides (15A)(15B)(as shown in the illustrative example of FIG. 15A). In further particular embodiments, one of each of the pair of ribs (38) can be correspondingly disposed on the second pair of the two pairs of opposed bracket sides (15B). In further particular embodiments, one each of the pair of ribs (33) can be correspondingly disposed on adjacent bracket sides (43A)(43B). In further embodiments, the pair of ribs can intersect. The first of a pair of ribs (38) can have a rib first end (40) disposed proximate the bracket body first end (10) and extending toward the bracket body second end (11). The second rib can intersect the first rib whether orthogonally or non-orthogonally.

Now referring generally to FIGS. 16A through 18B, particular embodiments of the recess element (24) can include a groove (44) disposed in the bracket body surface (18). The groove (44) can have a width (45) between the two groove edges (47) disposed on the bracket body surface (18). The width of the groove (44) being less than the distance (46) between the bracket body first end (10) and the bracket body second end (11). The groove (44) can further have a depth (48) between the two edges (47) of the groove (44) and the bottom (49) of the groove (44). The groove (44) can, but need not necessarily, extend between a pair of open groove ends (50A) (SOB) correspondingly disposed on the bracket body surface (18). The groove (44) can further have a location disposed medially on the bracket body surface (18) between the bracket base (4) and the bracket body second end (11). In particular embodiments, the groove (44) can circumferentially extend around the bracket body (5). In particular embodiments, the groove (44) in cross section orthogonal to the longitudinal axis can define a generally arcuate groove surface (51). The arcuate groove surface (51) can define an arc having an arc measure of about 45 degrees to about 180 degrees. In particular embodiments, the arc measure can be selected from the group including or consisting of: about 50 degrees to about 70 degrees, about 60 degrees to about 80 degrees, about 70 degrees to about 90 degrees, about 80 degrees to about 100 degrees, about 90 degrees to about 110 degrees, about 100 degrees to about 120 degrees, about 110 degrees to about 130 degrees, about 120 degrees to about 140 degrees, about 130 degrees to about 150 degrees, about 140 degrees to about 160 degrees, about 150 degrees to about 170 degrees, or combinations thereof.

In embodiments having two pairs of opposed bracket sides (15A) (15B), the bracket body (5) can have a groove (44) disposed in the bracket body surface (18). The groove (44) can extend between a pair of open groove ends (50A) (50B) correspondingly disposed at the bracket body surface (18). The pair of open groove ends (50A) (SOB) can further be correspondingly disposed at a first pair (31) of the two pairs of opposed bracket sides (15A) (15B) or disposed at a second pair (52) of the two pairs of opposed bracket sides (15A) (15B).

Figure 18A:
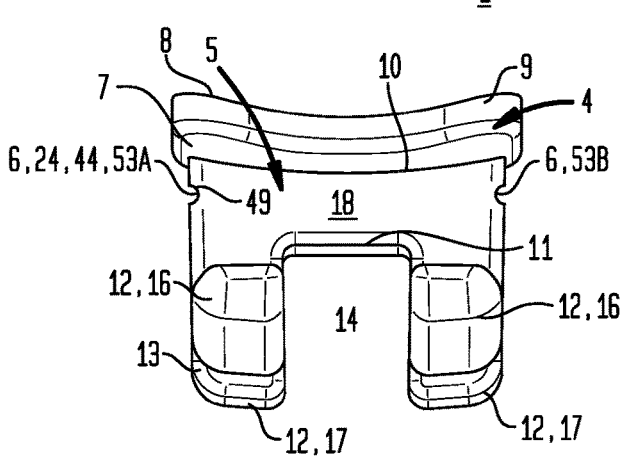
FIG. 18A is a front elevation view of another particular embodiment of a bracket including a bracket retention anchor.
Figure 18B:
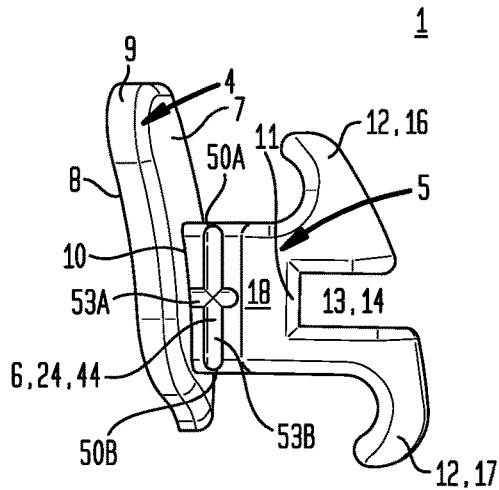
FIG. 18B is a side elevation view of another particular embodiment of a bracket including a bracket retention anchor.

Further embodiments of the recess element (24) can include a pair of grooves (53A) (53B). In embodiments of the bracket body (5) having two pairs of opposed bracket sides (15A) (15B), each one of the pair of grooves (53A) (53B) can be correspondingly disposed in the first pair (31) of the two pairs of opposed bracket sides (15A) (15B) or each one of the pair of grooves (53A) (53B) can be correspondingly disposed in the second pair (52) of the two pairs of opposed bracket sides (15A) (15B). In further particular embodiments, the pair of grooves (53A) (53B) can be correspondingly disposed one each in adjacent bracket sides (43). In further embodiments, the pair of grooves (53A) (53B) can intersect on the bracket body (5), as illustrated in FIGS. 18A and 18B. The first groove (53A) can have a first groove end (54) disposed proximate the bracket body first end (10) and the first groove (53A) can extend toward the bracket body second end (11), and the second groove (53B) can intersect the first groove (53B).

As can be easily understood from the foregoing, the basic concepts of the present invention may be embodied in a variety of ways. The invention involves numerous and varied embodiments of a bracket system and methods for making and using such bracket system including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "anchor" should be understood to encompass disclosure of the act of "anchoring"—whether explicitly discussed or not—and, conversely, were there effectively disclosure of the act of "anchoring", such a disclosure should be understood to encompass disclosure of an "anchor" and even a "means for anchoring." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) each of the brackets herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

What is claimed is:

1. An orthodontic system, comprising:
   one or more brackets, each including,
      a bracket base;
      a bracket body having a bracket body first end secured to said bracket base and having a bracket body second end terminating at a plurality of bracket heads defining an archwire slot;
      a bracket retention anchor disposed on said bracket body between said bracket body first end and said bracket body second end;
   a bonding tray configured to receive a plurality of teeth of a dental arch;
      wherein said bonding tray includes one or more cavities, each configured to correspondingly receive said one or more brackets;

wherein said one or more cavities each have a cavity wall configured to mateably engage said bracket retention anchor disposed on said bracket body;

wherein said cavity wall mateably engaged to said bracket retention anchor disposed on said bracket body increases resistance to movement of said one or more brackets in said bonding tray.

2. The bracket of claim 1, wherein said bracket retention anchor comprises a recess element disposed in said bracket body surface between said bracket body first end and said bracket body second end, said matrix material of said bonding tray disposed in said recess element to assist anchoring of said bracket in said matrix material of said bonding tray.

3. The bracket of claim 2, wherein said recess element comprises one or more indentations disposed in said bracket body surface.

4. The bracket of claim 2, wherein said recess element comprises a groove disposed in said bracket body surface.

5. The bracket of claim 4, wherein said groove extends between a pair of open groove ends correspondingly disposed at said bracket body surface.

6. The bracket of claim 5, wherein said groove disposed medially on said bracket body.

7. The bracket of claim 5, wherein said groove defines a generally arcuate groove surface.

8. The bracket of claim 7, wherein said arcuate groove surface defines an arc having an arc measure of about 45 degrees to about 180 degrees.

9. The bracket of claim 4, wherein said bracket body has two pairs of opposed bracket sides, said pair of open groove ends correspondingly disposed at a first pair of said two pairs of opposed bracket sides or disposed at a second pair of said two pairs of opposed bracket sides.

10. The bracket of claim 4, wherein said bracket body has two pairs of opposed bracket sides, wherein said groove comprises a pair of grooves one each of said pair of grooves correspondingly disposed in said first pair of opposed bracket sides or one each of said pair of grooves correspondingly disposed in said second pair of opposed bracket sides.

11. The bracket of claim 4, wherein said groove includes a pair of grooves, one each of said pair of grooves correspondingly disposed in adjacent bracket sides.

12. The bracket of claim 4, wherein said groove circumferentially extends around said bracket body.

13. The bracket of claim 4, wherein said groove comprises first and second grooves intersecting on said bracket body.

14. The bracket of claim 13, wherein said first groove has a first groove end disposed proximate said bracket body first end, said first groove extending toward said bracket body second end, wherein said second groove intersects said first groove.

15. The bracket of claim 2, wherein said recess element disposed in said bracket body surface between said bracket body first end and said bracket body second end comprises a first portion of said bracket body proximate said bracket base having a first width and a second portion of said bracket body distal said bracket base having a second width, said second width greater than said first width.

16. The bracket of claim 1, wherein said bracket retention anchor comprises a taper element, wherein at least one surface of said bracket body surfaces tapers approaching said bracket body first end, said matrix material of said bonding tray disposed about said taper element to assist positional anchoring of said bracket in said matrix material of said bonding tray.

17. The bracket of claim 16, wherein said bracket body has two pairs of opposed bracket sides, wherein each of a first pair of said opposed bracket sides taper approaching said bracket body first end.

18. The bracket of claim 16, wherein said bracket body has two pairs of opposed bracket sides, wherein each of said two pairs of opposed bracket sides taper approaching said bracket body first end.

19. The bracket of claim 18, wherein said taper element occurs proximate said bracket body first end.

20. The bracket of claim 1, wherein said bracket retention anchor comprises a projection element extending outward of said bracket body surface between said bracket body first end and said bracket body second end, said matrix material of said bonding tray disposed about said projection element to assist positional anchoring of said bracket in said matrix material of said bonding tray.

21. The bracket of claim 20, wherein said projection element comprises a rib disposed on said bracket body surface, said rib having an elongate rib body disposed between a rib first end and a rib second end.

22. The bracket of claim 21, wherein said rib disposed medially on said bracket body.

23. The bracket of claim 21, wherein an orthogonal cross-section to a longitudinal axis of said rib defines a generally arcuate rib surface.

24. The bracket of claim 23, wherein said arcuate rib surface defines an arc measure of about 45 degrees to about 180 degrees.

25. The bracket of claim 21, wherein said bracket body has two pairs of opposed bracket sides, wherein said rib comprises a pair of ribs, one each of said pair of ribs correspondingly disposed on said first pair of opposed bracket sides or one each of said pair of ribs correspondingly disposed on said second pair of opposed bracket sides.

26. The bracket of claim 21, wherein said rib comprises a pair of ribs one each of said pair of ribs correspondingly disposed on adjacent bracket sides.

27. The bracket of claim 21, wherein said rib circumferentially extends around said bracket body.

28. The bracket of claim 21, wherein said rib comprises a first and second rib intersection on said bracket body, wherein said first rib has a rib first end disposed proximate said bracket body first end and extending toward said bracket body second end, wherein said second rib intersects said first rib.

* * * * *